United States Patent [19]

Davis

[11] 4,407,300

[45] Oct. 4, 1983

[54] POTENTIOMETRIC DIAGNOSIS OF CANCER IN VIVO

[76] Inventor: Robert E. Davis, 125 Hillcrest Dr., Hinsdale, Ill. 60521

[21] Appl. No.: 168,018

[22] Filed: Jul. 14, 1980

[51] Int. Cl.³ .............................................. A61B 5/05
[52] U.S. Cl. ................................................... 128/734
[58] Field of Search ..................... 128/734, 630, 639

[56] References Cited

U.S. PATENT DOCUMENTS

| 3,834,374 | 9/1974 | Ensanian | 128/734 X |
| 4,184,486 | 1/1980 | Papa | 128/734 X |
| 4,291,708 | 9/1981 | Frei et al. | 128/734 |

FOREIGN PATENT DOCUMENTS 2424580 12/1975 Fed. Rep. of Germany ...... 128/734

OTHER PUBLICATIONS

Haseltine, "Quick, New, Painless Test . . . ", Wash. Post, Dec. 15, 1964.

Ash, "Detecting Electrical Change in Cancer", Research Disclosure, No. 142, p. 14, Feb. 1976.

*Primary Examiner*—Lee S. Cohen
*Attorney, Agent, or Firm*—Keil & Witherspoon

[57] ABSTRACT

Methods for scanning and diagnosing the presence or absence of malignant cancerous tissue in areas such as mammary tissue and lymph nodes of human and animal bodies by measuring the electromotive force generated by a platinum electrode or probe in contact with skin or subcutaneous portions of a body area to be diagnosed for presence or absence of said malignant tissue, and recording as suspect areas of malignant growth at least those body areas which were in contact with the probe or electrode when a significant negative electromotive force in the order of minus two millivolts or less was measured, the electromotive force being measured across two electrodes or probes, one in contact with normal skin or tissue, and the other in contact with skin or subcutaneous portions of the body area to be diagnosed.

3 Claims, No Drawings

POTENTIOMETRIC DIAGNOSIS OF CANCER IN VIVO

STATEMENT OF THE INVENTION

The subject invention relates to diagnosis techniques useful in the examination of human and animal bodies to detect the presence of carcinogenic tissue. The techniques measure electromotive forces generated by the body and use these measurements to distinguish the presence of cancerous tissue.

BACKGROUND

Electrical forces are generated by the body under normal, abnormal, and healing states of health. J. Watson and E. M. Downes, *Medical & Biological Engineering & Computing,* 17, 161-9, March, 1979, has summarized the status of various phenomena in the investigation of the electrical enhancement of bone healing. Compression of bones produces (via a piezoelectric effect) a local negative charge which is associated with osteoblastic activity and consequent bone deposition. Watson also reported the results of treatment for various types of bone-nonunion in eight patients in long-term clinical trials. Of these eight, six cases resulted in successful bone unions.

Metallic elements at low concentrations in living tissues are involved in a biochemical system which is capable of maintaining a measurable emf. The electrochemical nature of this system then plays a vital role in regulating the amount of growth as well as the rate of growth of new tissues—including hyperplasias and malignant neoplasms.

The results of preliminary studies in development of the invention indicate that cancerous tissues (human mammary tissues, human lymph-node tissues, and subcutaneously implanted mouse hepatomas) exhibit a small negative emf (a few millivolts) relative to "normal" tissues, e.g., skin. In subcutaneously implanted mouse hepatomas there is an asymmetric distribution of some metal atoms or ions (particularly zinc and iron) between the interior mushy tissue, the interior surface of the tumor's capsule, and the external surface of the tumor's capsule.

The primary advantages of the invention are the reproducibly reliable identification of malignant neoplastic cells and the speed (a few seconds per measurement) with which such differential identifications can be made. Histological examination of frozen tissue sections typically requires at least 20 minutes per specimen. This prolongs the time the patient must remain under anaesthesia.

The new hypothesis presented herein is that metallic elements and ions at low concentrations within cellular material are involved in a biochemical system which is capable of maintaining a measurable emf. Based on extensive understanding of well-known principles of catalysis and electrochemical technology, this new and unique hypothesis helps to explain the growth of neoplasms. This unusual synergistic combination of two entirely different disciplines with biochemistry has resulted in a new approach to research in tumor growth.

Normal concentrations of trace elements within humans and other animals are covered extensively by Underwood, *Trace Elements in Human and Animal Nutrition,* Academic Press, New York (1971). Publications covering specific elements and their effects in both normal and abnormal tissues are increasing. Fisher, "Function and Homeostesis of Copper and Zinc in Mammals", *The Science of the Total Environment,* 4:373 (1975) discusses primarily biomedical investigations involving Zn. Since then there have been major efforts directed at understanding the effects of Zn compounds on both normal and abnormal biological tissues. Several independent laboratories have reported many observations pertaining to Zn concentrations and correlations with reduced tumor growth, lower incidence of tumor development, and positive effects from various Zn treatments. Munro, H. N. and M. C. Lindner, "Ferritin: Structure, Biosynthesis, and Role in Iron Metabolism", *Physiological Reviews,* 58(2):317 (1978) and G. M. Williams, N. Hiortoa, and J. M. Rice, "The Resistance of Spontaneous Mouse Hepatocellular Neoplasm to Iron Accumulation During Rapid Iron Loading by Parenteral Administration and Their Transplantability", *American Journal of Pathology,* 94(1):65 (1979), report conflicting results on the effects of Fe treatment in cancerous cells.

Despite this extensive literature, little work has been reported pertaining to the actual chemical mechanisms involved in hyperplastic growth. Essentially no references specifically direct their major emphasis toward the electrochemical effects of such mechanisms. The importance of completely understanding these fundamental properties prompted the initial research studies resulting in the invention.

Based on the assumption that certain neoplastic activity could be microscopically catalyzed by the formation of localized electrochemical cells, experiments were designed to determine what chemical structures would be required. Conceptual models of a tumor structure with interior and exterior chemical systems having two different electrochemical potentials, which would produce a measurable, regulated emf across the capsule (or wall) of such a tumor, were deduced.

THE INVENTION

Briefly, the invention involves methods for scanning human and other animal bodies to diagnose the presence or absence of malignant cancerous tissue in various areas of the bodies. It involves measuring the electromotive force (emf) generated by a probe or electrode in contact with skin or subcutaneous portions of a body area to be diagnosed for the presence or absence of such tissue. A second probe or electrode is in contact with healthy, normal skin or other tissue of the person or animal. Suspect areas of malignant cancerous growth are recorded for those body areas in contact with the first-mentioned probe or electrode whenever a negative electromotive force of $-2$ millivolts (mv) or less was measured.

Areas of the human body in which the detection and diagnosis methods of the invention have proven to be useful include mammary tissue and lymph node tissue.

The probes or electrodes are made of readily sterilizable, inert, electrically conductive metals, e.g., platinum, silver or gold. Platinum wires, or platinum needles for subcutaneous probing, have proven to be reliable and relatively inexpensive probes or electrodes.

Any measured electromotive force is significant. As a practical matter, however, the base value for the measured emf at which malignant cancerous tissue is diagnosed and the areas involved are recorded, is in the order minus 2 mv or less, i.e., in the range of about $-2.0$ to about $-5.0$ mv.

Experimental Results

Initial experiments were conducted by measuring the small emf potentials of numerous mammary adenocarcinomas in ten volunteer patients. In all confirmed cases, a definite negative emf relative to skin ranging from 2.5 to 4.5 millivolts was recorded. Normal tissue showed either a positive or a nearly zero emf. Several hundred measurements were obtained from these patients. In large tumors the entire periphery of the tumor could be successfully mapped by recording the emf. In one patient, nearly 20 tumors were located and mapped.

Two different mouse hepatomas (H6 hepatomas in male mice of the strain A/J and BW 7756 hepatomas in male mice of the strain C57L/J) were serially transplanted subcutaneously in the lower back region through ten passages over nine months. These cancers, now thought to have reached "native" strength, beginning from the cells contained in 100–150 microliters of a hepatomas-cell-suspension, grow into an encapsulated tumor massing several grams which will kill the host mouse within approximately four weeks.

Forty-eight hepatomas were produced for experimentation. Capsule material surrounding the fluctuant or mushy interior tumor material was surgically removed using glass tools, stretched between two thin Mylar films, and analyzed using x-ray fluorescence. Analysis of one side thus provided information pertinent to the outer wall of the tumor capsule, and analysis of the other side provided information pertinent to the interior capsule wall which had been in direct contact with cancerous-cells. Analytical data obtained by integrating the signal during a 1000-second period (signal averaging) for several sets of samples strongly indicated new and interesting data.

The outer capsule wall surrounded by normal body tissue showed low Zn and high Fe similar to normal tissue. The interior walls showed unusually high levels of Zn and low levels of Fe. Based on a standard solution containing 20 ppm Zn, the Zn concentration was estimated at over 400 ppm. The mushy or fluctuant internal tumorous material showed the lowest concentration of Zn and low levels of Fe. These data were correlated with the basic hypothesis that a concentration gradient of two metals with different electrochemical potentials would create a measurable emf. The concentration gradient of Fe and Zn experimentally measured by X-ray fluorescence and their respective oxidation potentials were utilized in the Nernst equation to calculate the resulting emf as shown below.

Nernst Equation: $\text{emf} = E_i = E^o + \frac{RT}{nF} \ln \frac{[\text{Oxidized}]}{[\text{Reduced}]}$ For a concentration cell with $n=1$ (for $Fe^{+3}$):

$$E_{cell} = 0.0591 \log \frac{[Fe^{+3}] \text{ outside}}{[Fe^{+3}] \text{ inside}} = 0.0591 \log \left(\frac{3.83}{3.28}\right)$$

$$= (0.0591)(0.0673) = +0.00398 \text{ Volts} = 3.98 \text{ mV}$$

Hence, the outside is 3.98 mV more positive than the inside of the capsule. Note that this calculated value remarkably approximates the average emf measured for the mammary adenocarcinomas.

Strong support for the hypothesis of the invention has been obtained from the nearly perfect correlation observed between emf measurements across normal and cancerous tissue and routine histopathological examination. The significant benefit immediately realizable from utilization of diagnostic emf measurements derives from the fact that it yields instantaneous and unambiguous results. Its use in the surgical theater could save the 20–30 minutes per biopsy now required by an oncologist for histopathological evaluation during the course of cancer surgeries.

I claim:

1. A method for scanning and diagnosing the absence or presence and location of malignant cancerous tissue in an area of the body comprising: measuring the presence or absence of a naturally-occurring electromotive force between a first probe in contact with the skin or subcutaneous portions of a body area to be diagnosed for the presence or absence of said malignant tissue, and a second probe which is maintained in contact with an area of normal body tissue, and recording as suspect, areas of malignant growth, at least those body areas which were in contact with said first probe when an electromotive force between −2.0 and −5.0 mv was measured, wherein said naturally-occurring electromotive force arises from an asymetrical distribution of metal atoms or ions about the suspected malignant tissue.

2. A method as claimed in claim 1, wherein the said body area comprises human mammary tissue.

3. A method as claimed in claim 1, wherein said body area comprises human lymph node tissue.

* * * * *